US009600636B2

United States Patent
Xu et al.

(10) Patent No.: US 9,600,636 B2
(45) Date of Patent: Mar. 21, 2017

(54) MEDICATION COMPLIANCE CAPPING SYSTEM, ASSEMBLY, AND METHOD

(71) Applicants: Tao Xu, Naperville, IL (US); Xiaojun Zhang, Shenzhen (CN); Linzhi Fang, Shenzhen (CN)

(72) Inventors: Tao Xu, Naperville, IL (US); Xiaojun Zhang, Shenzhen (CN); Linzhi Fang, Shenzhen (CN)

(*) Notice: Subject to any disclaimer, the term of this patent is extended or adjusted under 35 U.S.C. 154(b) by 0 days.

(21) Appl. No.: 14/633,270

(22) Filed: Feb. 27, 2015

(65) Prior Publication Data

US 2016/0253477 A1   Sep. 1, 2016

(51) Int. Cl.
G08B 21/00 (2006.01)
G06F 19/00 (2011.01)
A61J 7/04 (2006.01)

(52) U.S. Cl.
CPC ............ *G06F 19/3462* (2013.01); *A61J 7/04* (2013.01)

(58) Field of Classification Search
CPC . A61J 7/0481; A61J 7/084; A61J 1/14; G08B 21/24; G08B 1/08
USPC .... 340/573.1, 309.16, 540, 321, 531, 309.7; 221/2; 368/10, 107, 204
See application file for complete search history.

(56) References Cited

U.S. PATENT DOCUMENTS

| 4,156,489 A * | 5/1979 | Kong | B65D 50/045 215/214 |
|---|---|---|---|
| 4,504,153 A * | 3/1985 | Schollmeyer | A61J 7/0481 221/2 |
| 4,847,597 A * | 7/1989 | Dobosi | B65D 51/248 206/459.1 |
| 5,408,443 A * | 4/1995 | Weinberger | A61J 7/0481 221/3 |
| 5,642,731 A * | 7/1997 | Kehr | A61J 7/0481 600/300 |
| 5,852,590 A * | 12/1998 | de la Huerga | A61J 7/0481 368/10 |
| 6,084,504 A * | 7/2000 | Rosche | A61J 7/0472 222/638 |
| 6,259,654 B1 * | 7/2001 | de la Huerga | A61J 7/0084 368/10 |
| 6,529,446 B1 * | 3/2003 | de la Huerga | A61J 7/0084 368/10 |

(Continued)

*Primary Examiner* — Hoi Lau
(74) *Attorney, Agent, or Firm* — Christopher J. Scott

(57) ABSTRACT

A medication compliance cap system, cap assembly, and associated methodology enhance compliance of a user's prescribed or scheduled medication regimen. Central to these specifications is a "smart" or intelligent medication cap assembly that basically functions to communicate wirelessly with a remote medication compliance application or software executable via a personal computing device. A power source and signal-generating circuitry are housed within an inner cap housing and an outer cap housing, which circuitry is selectively switched on and/or off via engagement with an upper container rim of a medication container. The medication compliance application schedules medication-taking events and alerts the user when a medication-taking event is due. The user may stop the alert by removing the medication cap assembly from a medication container, at which time an alert cessation signal is transmitted to the medication compliance application.

19 Claims, 9 Drawing Sheets

(56) References Cited

U.S. PATENT DOCUMENTS

| | | | | |
|---|---|---|---|---|
| 6,667,936 B1* | 12/2003 | Ditzig | A61J 7/0409 368/10 |
| 7,715,277 B2* | 5/2010 | de la Huerga | A61J 7/0084 221/2 |
| 7,821,404 B2* | 10/2010 | Walker | A61J 7/0481 340/321 |
| 8,055,509 B1* | 11/2011 | Walker | G06F 19/3462 128/898 |
| 8,193,918 B1* | 6/2012 | Shavelsky | A61J 7/04 340/309.16 |
| 8,269,613 B2* | 9/2012 | Lazar | A61J 7/0481 340/309.16 |
| 8,319,613 B2* | 11/2012 | Lazar | A61J 1/14 340/309.16 |
| 8,446,799 B2* | 5/2013 | Burke, Jr. | G04F 8/08 368/10 |
| 9,211,233 B2* | 12/2015 | Shavelsky | A61J 7/04 |
| 2001/0017817 A1* | 8/2001 | De La Huerga | A61J 1/035 368/10 |
| 2001/0028308 A1* | 10/2001 | De La Huerga | A61M 5/14212 340/573.1 |
| 2003/0063522 A1* | 4/2003 | Sagar | A61J 7/0481 368/10 |
| 2004/0201458 A1* | 10/2004 | Rosche | A61J 7/0472 340/309.16 |
| 2005/0088289 A1* | 4/2005 | Rochkind | G08B 21/24 340/309.16 |
| 2005/0151625 A1* | 7/2005 | Lai | A61J 7/0409 340/309.16 |
| 2006/0139151 A1* | 6/2006 | Rosche | A61J 7/0481 340/309.16 |
| 2006/0152364 A1* | 7/2006 | Walton | B65D 55/028 340/568.1 |
| 2006/0256664 A1* | 11/2006 | Varon | B65D 79/02 368/89 |
| 2007/0014191 A1* | 1/2007 | Brandon | A61J 7/0472 368/10 |
| 2008/0136629 A1* | 6/2008 | Mahoney | G08B 1/08 340/540 |
| 2009/0040874 A1* | 2/2009 | Rooney | A61J 7/0472 368/10 |
| 2009/0200327 A1* | 8/2009 | Jurkovich | A61J 7/0409 221/3 |
| 2009/0281657 A1* | 11/2009 | Gak | A61J 7/0481 700/242 |
| 2009/0284355 A1* | 11/2009 | Kiran | A61J 7/0472 340/309.16 |
| 2009/0294521 A1* | 12/2009 | de la Huerga | A61J 1/035 235/375 |
| 2011/0227734 A1* | 9/2011 | Ortenzi | G08B 13/1436 340/568.1 |
| 2011/0253586 A1* | 10/2011 | Metry | A61J 7/0481 206/531 |
| 2012/0224458 A1* | 9/2012 | Burke, Jr. | G04F 8/08 368/10 |
| 2013/0002795 A1* | 1/2013 | Shavelsky | A61J 7/04 348/14.01 |
| 2014/0130453 A1* | 5/2014 | Shalala | B65B 7/28 53/420 |

\* cited by examiner

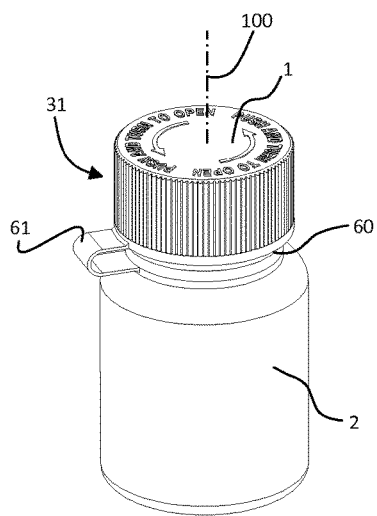
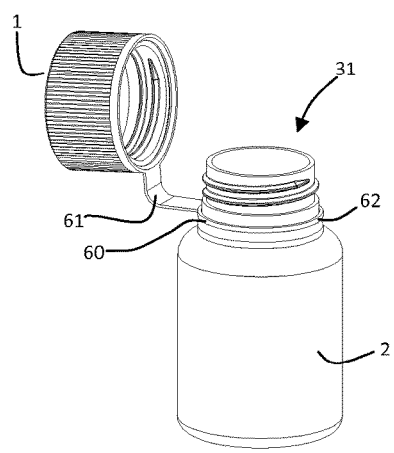
FIG. 1
FIG. 2
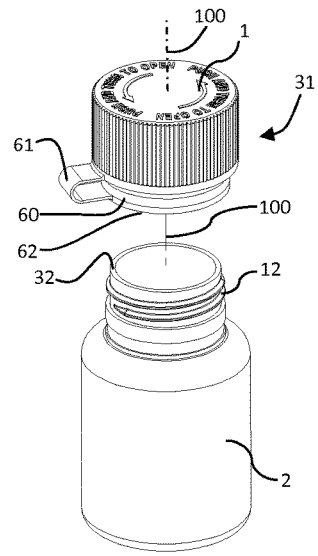
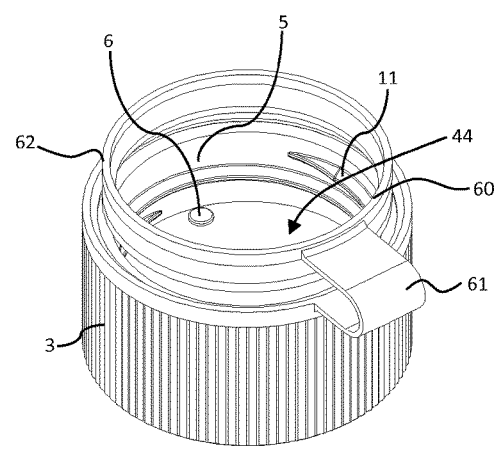
FIG. 3
FIG.4
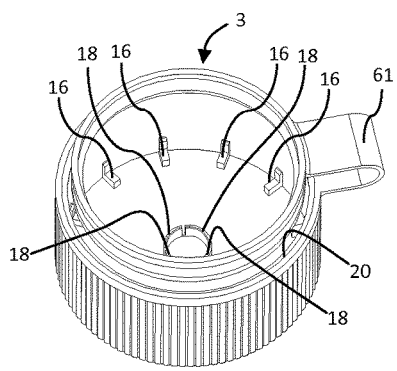
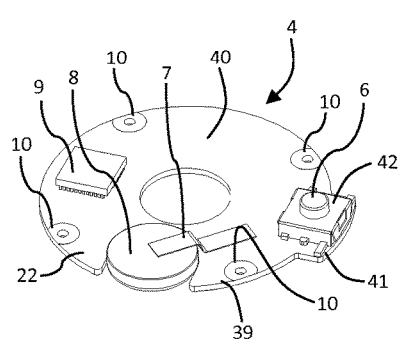
FIG. 5
FIG. 6

MEDICATION COMPLIANCE CAPPING SYSTEM, ASSEMBLY, AND METHOD

BACKGROUND OF THE INVENTION

Field of the Invention

The present invention generally relates to the field of medication container assemblies, and more particularly to a medication cap assembly having means for wirelessly communicating with remote personal communication or computing devices.

SUMMARY OF THE INVENTION

The present invention is primarily designed to enable users to follow an on-time and correct medication prescription regimen as may typically be the case with patients or the elderly. The system may preferably include or comprise (1) a smart medication cap assembly having wireless communication means for transmitting a (radio) signal when it is removed from a medication container, (2) a device that can receive this radio signal and/or send this signal to a smart phone or similar other mobile or personal computing device (e.g. through Bluetooth or Wi-Fi), and (3) a mobile application on a such a personal computing device that operates to remind patients or the elderly via an alert or alarm to adhere to their prescribed medication regimen, which alert or alarm may be stopped or ceased by a signal transmitted from the medication cap assembly when the same is removed from a medication container.

The system according to the present invention basically operates as follows: specific types of medications in the form of pills are placed in a medication container and the container is outfitted with the medication cap assembly according to the present invention. These types of medication containers may be typically distributed to the patient by way of a medication dispensary. A medication compliance mobile application may then be used to link the medication cap assembly to the particular medication housed within the medication container.

The medication compliance mobile application may then be programmed to set up a medication schedule, including days and times for taking the medication. According to the programmed schedule, the personal computing or communications device via the medication compliance application, will alarm or alert the patient or senior that the time has arrived to take his or her medication. The alarm may be provided until the patient opens the medication container, at which time a signal is sent to the device, and the alert or alarm is prompted to cease via the transmitted signal.

Other features and objects of our present invention will become more evident from a consideration of the following brief descriptions of patent drawings submitted in support of these specifications.

BRIEF DESCRIPTION OF THE DRAWINGS

FIG. 1 is a top perspective of the medication cap assembly according to the present invention attached to or assembled with a medication container and shown in a closed condition.

FIG. 2 is a top perspective of the medication cap assembly according to the present invention attached to or assembled with a medication container and shown in an open condition.

FIG. 3 is a top perspective of the medication cap assembly according to the present invention in exploded relation to a medication container.

FIG. 4 is a bottom perspective view of the medication cap assembly according to the present invention.

FIG. 5 is a bottom perspective view of an outer cap housing of the medication cap assembly according to the present invention showing a series of ribs and skirts for providing a childproof function of the cap assembly.

FIG. 6 is a bottom perspective view of the Printed Circuit Board assembly of the medication cap assembly for generating wireless communication signals according to the present invention.

DETAILED DESCRIPTION OF THE PREFERRED EMBODIMENT

Figure 7:
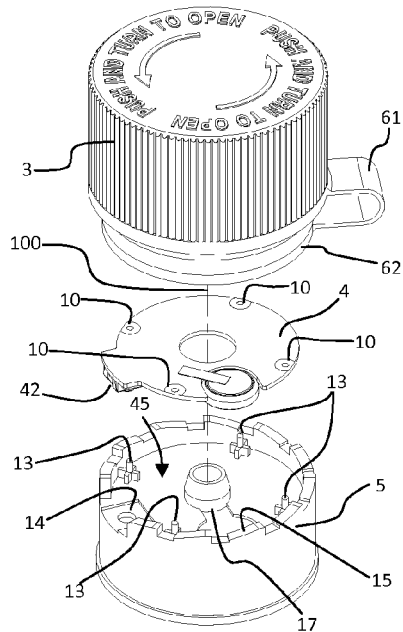
FIG. 7 is a first top exploded perspective view of the medication cap assembly according to the present invention.
Figure 8:
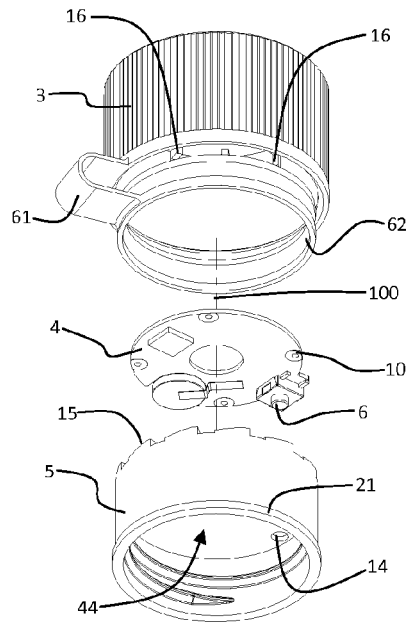
FIG. 8 is a first bottom exploded perspective view of the medication cap assembly according to the present invention.
Figure 9:
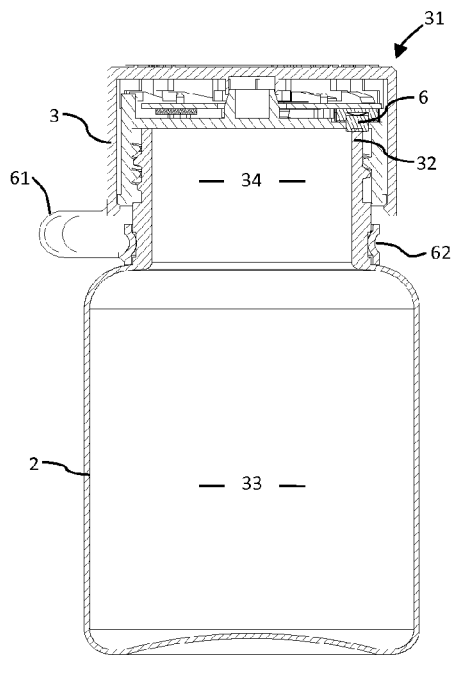
FIG. 9 is a first longitudinal cross-sectional view of the medication cap assembly assembled to a medication container showing the cap assembly in a closed position with the switch button of the Printed Circuit Board assembly in a depressed configuration.
Figure 10:
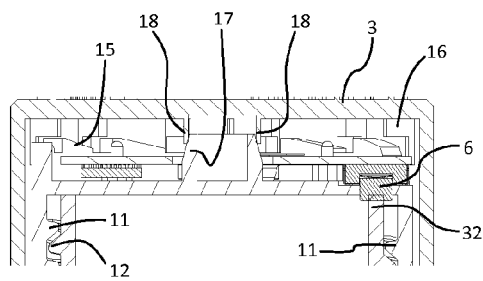
FIG. 10 is a first enlarged longitudinal cross-sectional view of the medication cap assembly attached to an upper portion of the medication container in the closed position showing skirt portions of the outer cap housing contacting a post portion of the inner cap housing.
Figure 11:
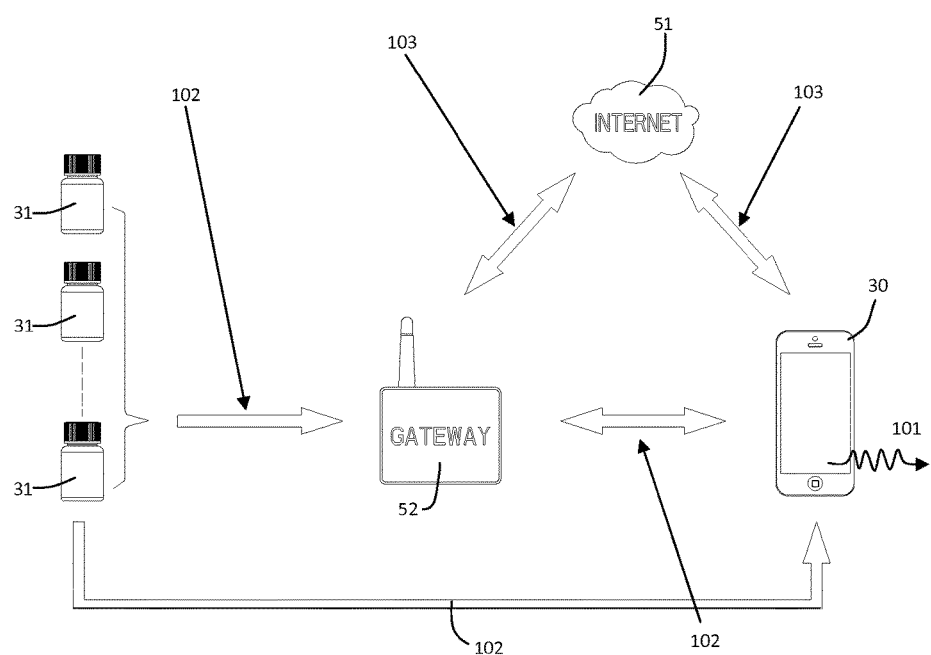
FIG. 11 is a schematic type drawing to show communication capabilities among the medication cap assembly, an Internet gateway, the Internet, and a personal computing or communications device.
Figure 12:
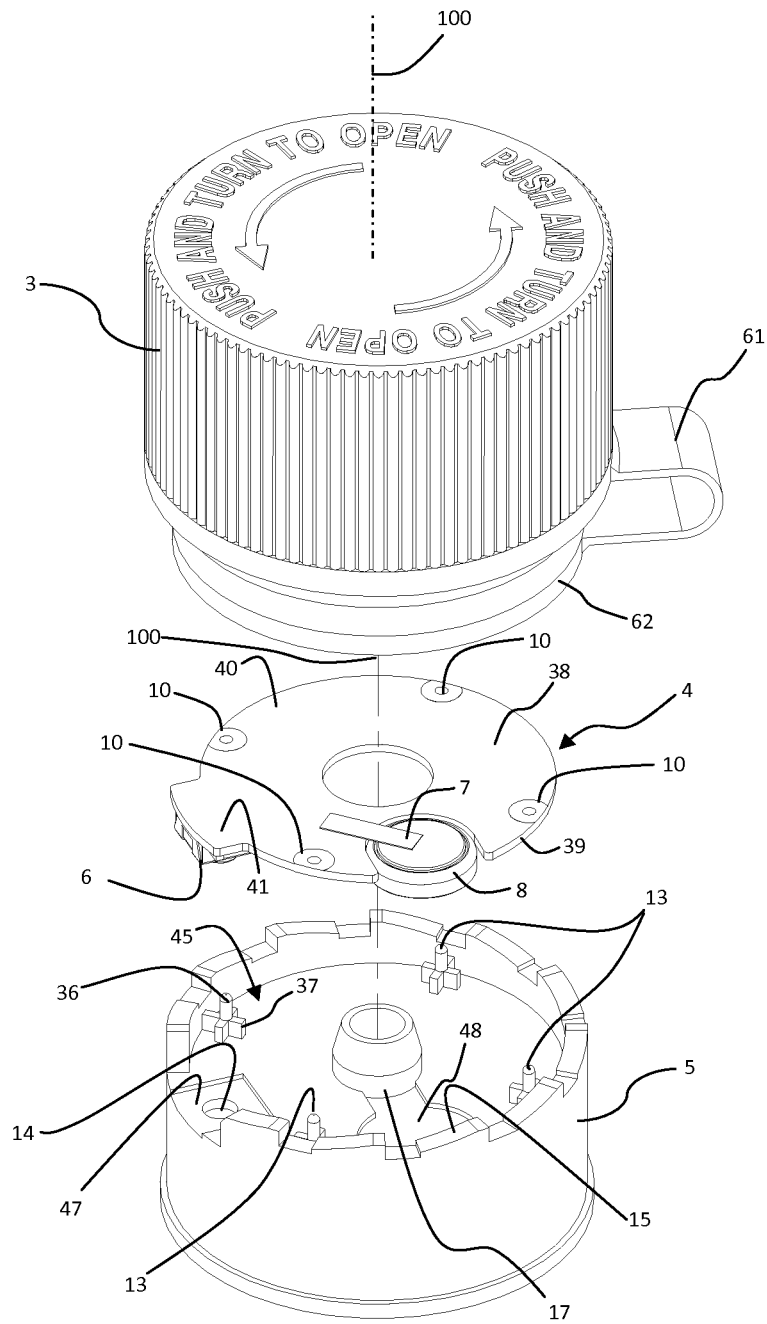
FIG. 12 is a second enlarged top exploded perspective view of the medication cap assembly according to the present invention, the view being enlarged from FIG. 6 to show in greater detail structures associated therewith.
Figure 13:
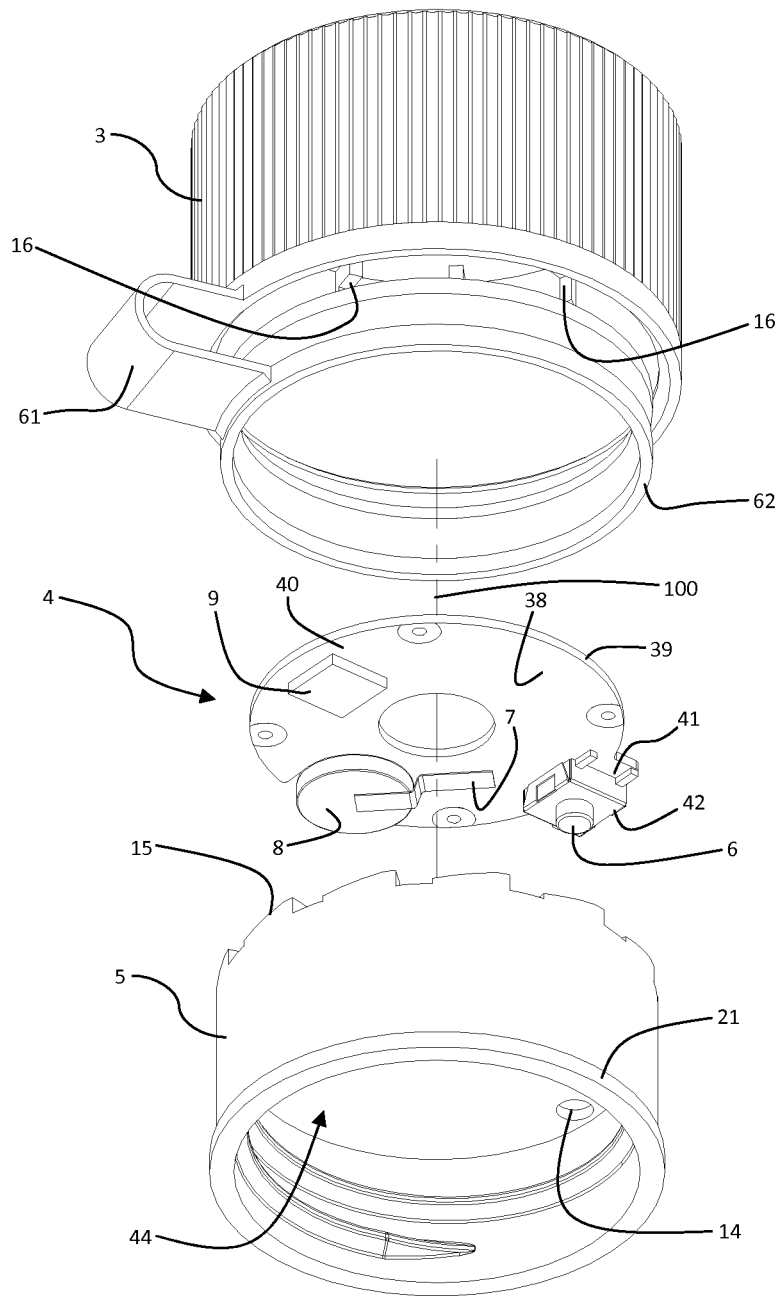
FIG. 13 is a second enlarged bottom exploded perspective view of the medication cap assembly according to the present invention, the view being enlarged from FIG. 7 to show in greater detail structures associated therewith.
Figure 14:
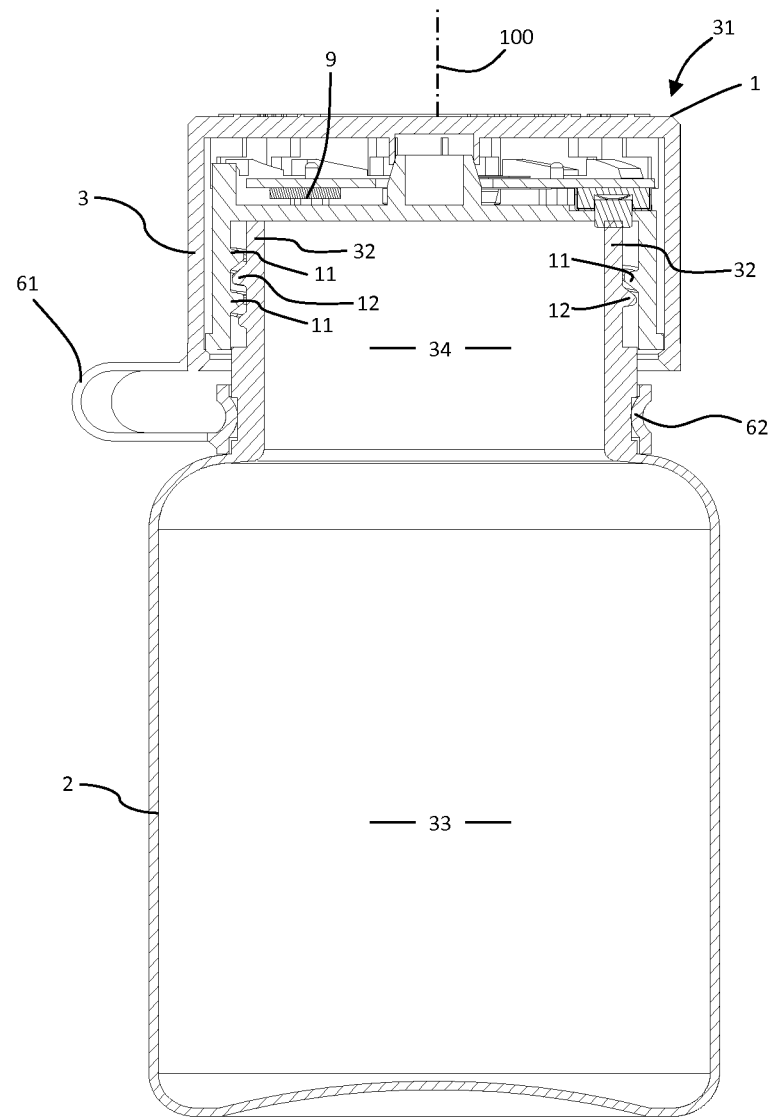
FIG. 14 is a second enlarged longitudinal cross-sectional view of the medication cap assembly assembled to a medication container showing the cap assembly in a closed position with the switch button of the Printed Circuit Board assembly in a depressed configuration, the view being enlarged from FIG. 8 to show in greater detail structures associated therewith.
Figure 15:
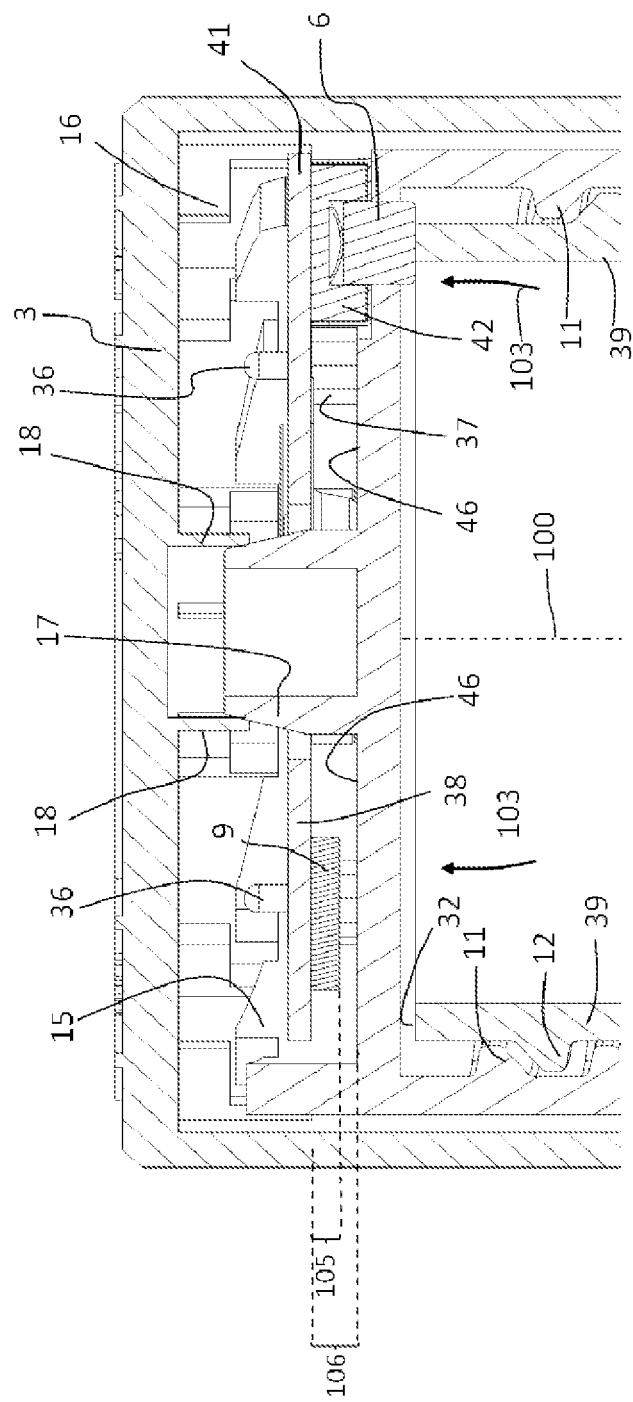
FIG. 15 is a second enlarged longitudinal cross-sectional view of the medication cap assembly attached to an upper portion of the medication container in the closed position, the view being enlarged from FIG. 9 to show in greater detail structures associated therewith.

Referring now the drawings with more specificity, the preferred embodiment of the present invention basically provides a so-called "smart" cap or medication container cap assembly as referenced at 1, which cap assembly 1 is communicable with a medication compliance mobile application supported or operated by a mobile computing device as exemplified by a user's "smart" phone or similar other mobile computing device as generically depicted and referenced at 30 communicable with the Internet as at cloud 51 or an Internet gateway as at box 52 via certain wireless technology including local wireless networks and/or cellular type communications as generically referenced at arrows 110.

Viewed or considered systemically, the present invention may thus be said to provide a medication compliance system for enhancing compliance of a user's prescribed medication regimen, which medication compliance system comprises, in combination, a medication compliance mobile application and a medication container assembly 31. The mobile medication compliance application is preferably operable via a mobile computing device as generically depicted and referenced at 30.

The medication container assembly 31 according to the present invention is believed to preferably comprise a medication container as referenced at 2 and the smart cap assembly 1. The medication container 2 may be preferably provided by medication dispensaries such as pharmacies and the like. To be operable with the smart cap assembly 1 according to the present invention, the medication container 2 may essentially comprise an upper container portion 34 for engaging the cap assembly 1 and a lower container portion 33 for housing medication(s). The upper container portion 34 may preferably comprise an upper container rim as at 32, and external threads as at 12 for threadably engaging internal threads as at 11 formed on an inner cap housing construction as at 5. The cap assembly 1 is thus rotatable about cap axis 100 for threadably attachment to the medication container 2.

Notably, the smart cap assembly 1 according to the present invention preferably and essentially comprises certain wireless communication means for wirelessly communicating with the medication compliance mobile application. The wireless communication means according to the present invention may be preferably exemplified by a Printed Circuit Board or PCB assembly as referenced at 4.

The medication compliance mobile application operable via the mobile computing device 30 basically functions to alert (e.g. visually, audibly or via tactile sensation (e.g. vibration)) the user when medication is to be retrieved from the medication container 2 assembly via an alert (e.g. visual, audible or tactile) as generically and diagrammatically depicted at arrow 101. The alert may be continuously or periodically provided until the smart cap assembly 1 is removed from the medication container 2.

When removed from the medication container 2, the smart cap assembly 1 (radio) transmits an alert cessation signal (as at arrow 102) via the wireless communication means the medication compliance mobile application to prompt an alert cessation or to otherwise cease the alert 101. In other words, when the alert 101 is perceived, the user may thus proceed to comply with the prescribed medication regimen by taking medication from the medication container 2 by first removing the cap assembly 1, which wireless alert cessation signals or triggers the medication compliance application to cease the alert 101.

The smart cap assembly 1 preferably comprises an outer cap housing as referenced at 3, the PCB assembly as referenced at 4, and an inner cap housing as referenced at 5. The PCB assembly 4 is preferably mounted on the topside of or in adjacency to an upper housing surfacing 35 of the inner cap housing 5 by via a plurality of post constructions 13, which post constructions preferably comprise an upper post portion as at 36 and a lower or basal spacer portion as at 37.

The smart cap assembly 1 may further preferably comprise a cap-to-container fastener assembly 60 comprising a tether element as at 61 and a neck-encircling ring construction as at 62. The tether element 61 extends from the ring construction 62, and is integrally formed with the outer cap housing 3 for tethering the smart cap assembly 1 ring construction 62. The ring construction 62 encircles the container neck in inferior adjacency to threads 12 for connecting the assembly 60 to the container 2. Thus, it is believed that assembly 60 functions to prevent inadvertent disassembly or loss of the smart cap assembly 1 relative to the container 2.

The upper post portions 36 of the post constructions 13 are preferably matable with peripherally located and substantially equally and circumferentially spaced apertures 10 formed in or through a PCB board or body portion 22 of the PCB assembly 4. In other words, the apertures 10, preferably numbering four, are spaced at 90 degree intervals around the perimeter 39 of a circular portion 40 of the board portion 22. A projected portion 41 preferably extends outward radially from the circular portion 40 for mounting a button assembly having a spring-biased button 6 and a button-centering housing 42.

Figure 16A:
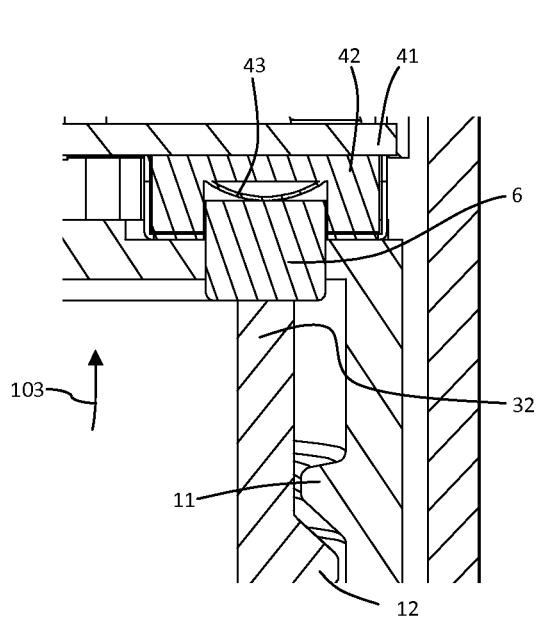
FIG. 16A is a sequentially first enlarged fragmentary depiction of the button assembly of the Printed Circuit Board assembly of the medication cap assembly according to the present invention showing the switch button in an actuated depressed configuration as depressed by the upper rim of the medication container.
Figure 16B:
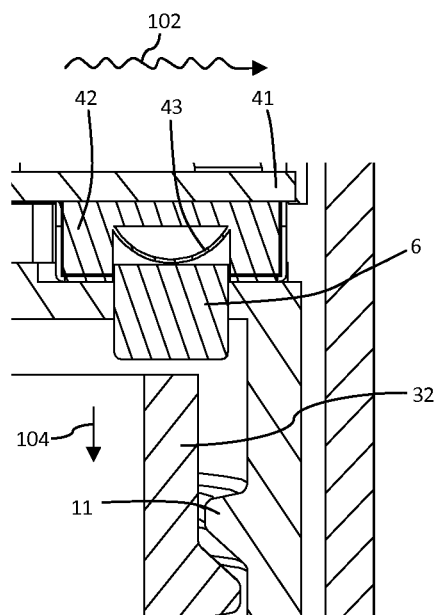
FIG. 16B is a sequentially second enlarged fragmentary depiction of the button assembly of the Printed Circuit Board assembly of the medication cap assembly according to the present invention showing the switch button in a relaxed configuration as the medication container disengages the switch button for initiating signal generation.

The button 6 is resiliently depressed and thus actuated via a spring element as at 43 as engaged by the upper container rim 32 as generally and comparatively depicted in FIGS. 16A and 16B. PCB assembly 4 may thus be said to preferably comprise PCB body or board portion 22, a switch button 6, a battery contact plate as at 7, a power source as exemplified by a button cell battery as at 8, a signal-transmitting Integrated Chip or IC as at 9 (for preferably generating (a radio type) signal 102) and other components (not specifically illustrated).

The inner cap housing 5 is assembled into the outer cap housing 3 with the cooperative engagement of a rim hook 20 formed on the outer cap housing 3 and a flange element 21 formed on the inner cap housing 5. The inner cap housing 5 is able to rotate inside the outer cap housing 3. The inner cap housing 5 is rotatable relative to the upper container portion 34 as threads 11 and 12 engage one another for axially displacing the upper container rim 32 into (as at arrow 103) and out of (as at arrow 104) engagement with button 6.

The outer cap housing 3 preferably comprises a group of ribs as at 16 and a series of four skirts as at 18 formed on the top inner side of the housing 3. The inner cap housing 5 preferably comprises a series of four post constructions 13, a button-letting aperture as at 14 for receiving an enabling axial displacement of the switch button 6, a group of gears as at 15, and a center post as at 17. Together the ribs 16, skirts 18, gears 15, and center post 17 function to provide a childproof function to the cap assembly according 1 to the present invention.

The switch button 6 of the button assembly of the PCB assembly 4 preferably protrudes and is axially displaceable through the button-letting aperture 14 on the inner cap housing 5. The skirts 18 formed on the outer cap housing 3 preferably mate with the post 17 formed on the inner cap housing 5 to create a spring force. The medication container 2 preferably comprises a container neck or upper container portion 34 having an upper container rim 32. As earlier described, the upper container rim 32 engages and disengages the switch button 6 for activating a signal 102 via the IC 9 of the PCB assembly 4, which preferably exemplifies the wireless communication means according to the present invention.

While the foregoing specifications set forth certain specificity, the same should not be construed as setting forth limits to the invention but rather as setting forth certain preferred embodiments and features. For example, as prefaced hereinabove, it is contemplated that the present invention essentially provides a so-called "smart" cap assembly for enhancing or supporting a medication compliance system or for generally enhancing compliance of a user's prescribed medication regimen.

Viewed systemically, the medication compliance system according to the present invention may be said to comprise in combination a medication compliance (mobile) software application executable, operable or supportable via a (mobile) computing device such as a "smart" phone, personal computing tablet or notebook computer, or similar other mobile computing device as at 30, and a medication cap assembly as at 2.

The medication container cap assembly, the medication container cap assembly preferably and essentially comprises certain wireless communication means as exemplified hereinabove for wirelessly communicating with the medication compliance mobile application. The medication compliance mobile application basically functions to alert the user when medication is to be retrieved from a medication container outfitted with the "smart" or intelligent cap assembly 2 or cap assembly 2 having means for communicating remotely with a personal computing device.

The alert may be preferably provided (singularly, periodically, or continuously) via the mobile application and the device 30 until the "smart" cap assembly is removed from the medication container 1. The "smart" cap assembly 2 preferably signals (as at 102) via the wireless communication means the medication compliance mobile application operable via the device 30 to cease or stop the alert 101 when the cap assembly 1 is made selectively interactive with the medication container 2.

Stated more particularly, the wireless communication means preferably signal or prompt an alert cessation via the medication compliance mobile application when the cap assembly is removed from the medication container 1. In this regard, it will be recalled that the medication container 1 preferably comprises an upper container portion having a container rim 32, which container rim 32 is engageable with the wireless communication means (e.g. via switch button 6) or resetting the cap assembly 1 when the medication container 2 is outfitted with the cap assembly 1.

In other words, the wireless communication means engages the medication container 2 or rim 32 when the cap assembly 1 is attached to the medication container 2. The cap assembly 1 preferably comprises an inner cap housing 5 and an outer cap housing 3. The inner cap housing 5 and the outer cap housing 3 are preferably cooperable to position portions of the wireless communication means relative to the medication container 2 for engagement and disengagement of the certain portions of the wireless communications means via the mediation container 2. The wireless communication means preferably engage the medication container via an aperture 14 formed the inner cap housing 5 when the cap assembly 1 is attached to the medication container 2.

The medication cap assembly may thus be said to enhance compliance of a user's (prescribed) medication regimen. To achieve this primary object, the medication cap assembly 1 according to the present invention essentially comprises wireless communication means for (a) wirelessly communicating with a medication compliance mobile application, and (b) signaling the medication compliance mobile application when selectively the cap assembly is selectively interactive with (e.g. placed into engagement with or disengaged from) a medication container 2.

The wireless communication means preferably signal an alert cessation via the medication compliance mobile application when the cap assembly 1 is removed from the medication container 2. The inner cap housing 5 of the cap assembly 1 is rotatable relative to the outer cap housing 3, and the wireless communication means are preferably rotatably fixed relative to the inner cap housing 5.

The inner cap housing 5 preferably comprises lower housing surfacing as at 44 and upper housing surfacing as at 45 with the button-letting aperture 14 extending intermediate the lower and upper housing surfacing 44-45. The lower housing surfacing preferably comprises internal threads as at 11. The upper housing surfacing 45 preferably comprises at least one, but preferably a series of post construction(s) 13. Each post construction is preferably matable with at least one post-receiving means (e.g. aperture(s) 10) cooperably associated with the wireless communication means for preventing rotation of the wireless communication means relative to the inner cap housing 5.

Each post construction 13 preferably comprises an upper post portion as at 36 and a lower spacer portion as at 37. The spacer portion(s) 37 basically function to engage planar portion 46 of the upper housing surface 45 and space portions of the wireless communications means therefrom. In this regard, it will be noted that the IC 9 comprises a certain thickness as at 105. The thickness 105 is preferably less than the height 106 of the spacer portions 37, and thus the spacer portions 37 help maintain a uniform distance between (planar) board portion 38 and the planar portion 46.

The four post constructions 13 are preferably equally circumferentially spaced from each other at 90 degree intervals at a periphery 39 of the upper housing surface 45. The upper housing surface 45 further preferably comprises at least two pocket constructions, which pocket constructions include a button-assembly-receiving pocket 47 and a power source-receiving pocket 48. The pocket constructions are preferably and respectively spaced intermediate a select three of the four post constructions for pocket-receiving assembly portions (i.e. the button assembly and/or the power source assembly) of the wireless communications means.

Figure 18:
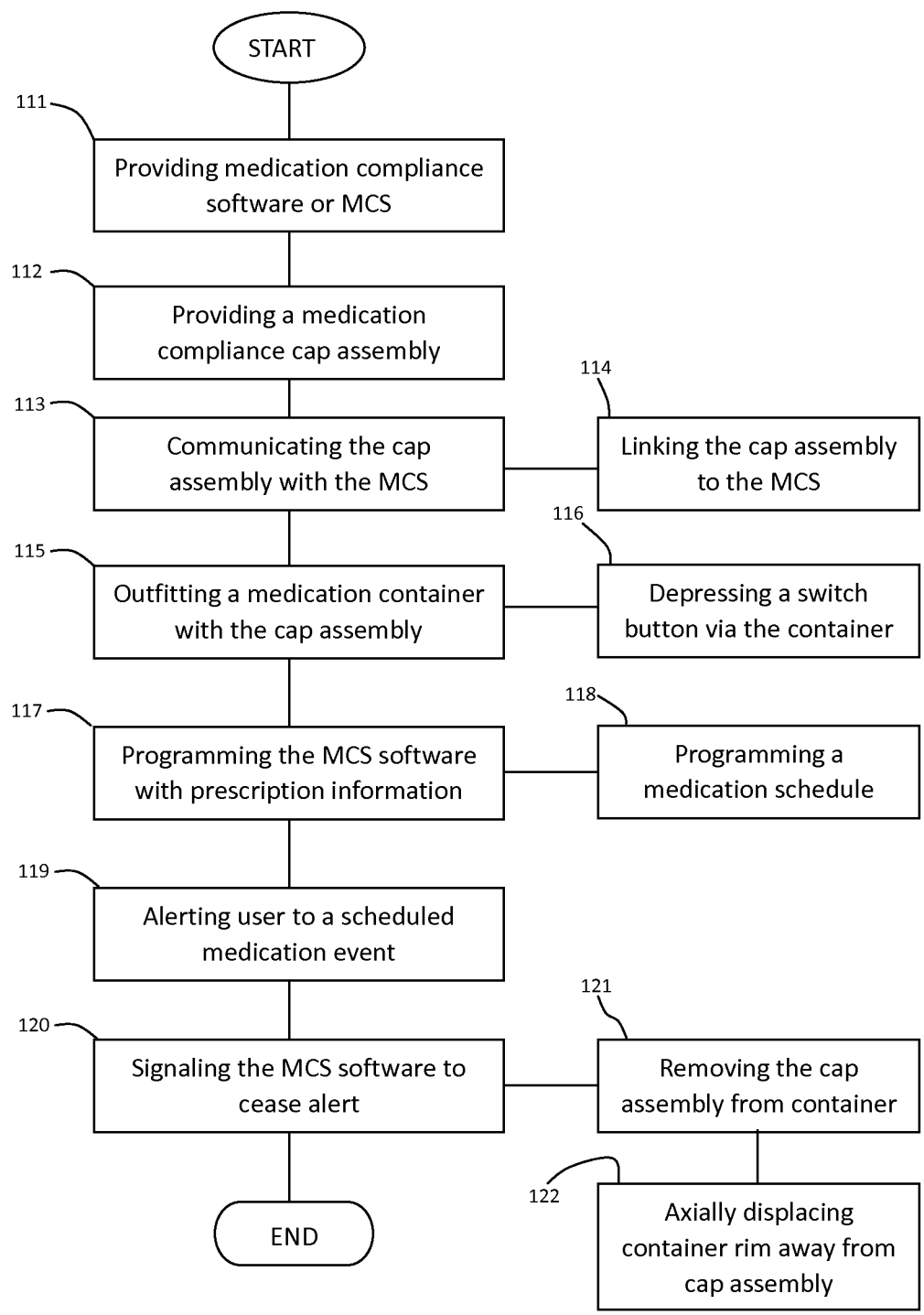
FIG. 18 is a simplified flowchart type diagram of certain medication compliance methodology according to or associated with the present invention.

The foregoing structural specifications are further believed to support certain medication compliance methodology for enhancing compliance of a user's (prescribed) medication regimen as generally diagrammed in FIG. 18. In this regard, the medication compliance method according to the present invention may be said to comprise the step (as at step or routine 111) of providing a medication compliance mobile application or certain medication compliance software, which medication compliance application or software is executable, operable, or supportable via a mobile or personal computing device as generically referenced at 30.

A medication cap assembly 1 is also provided (as at step or routine 112), which cap assembly comprises certain wireless communication means for wirelessly communicating (as at step or routine 113) (via signal transmission 102) with the medication compliance application once linked therewith (as at subroutine 114).

The medication compliance method may further preferably comprise the steps of outfitting a medication container 2 with the medication cap assembly 1 (as at step or routine 115) (thereby depressing switch button 6 and activating or re-setting the cap assembly 1 (as at step or subroutine 116)); and programming the medication compliance application with prescription medication regimen information (as at step or routine 117) (such as scheduling days and times the medication is to be taken) as typically provided to the user from labeling on the mediation container 1.

Figure 17:
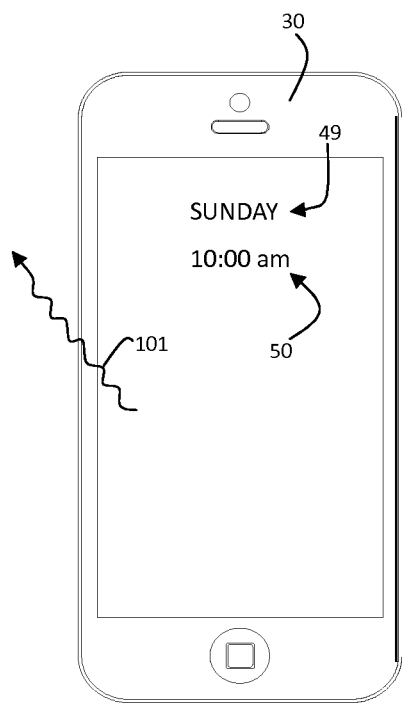
FIG. 17 is an enlarged anterior plan view of a generic personal computing or communications device showing a date and time and generic alert signal emanating therefrom.

In other words, the step of programming the medication compliance application with prescription medication regimen information from the mediation container may further preferably comprise the step of programming a medication schedule (as at step or subroutine 118), the medication compliance mobile application comprising or otherwise being cooperable with a clock function upon the device 30, which clock function provides day and time information as at day information (e.g. Sunday) 49 and time information (e.g. 10:00 am) 50, respectively in FIG. 17.

The medication compliance method may further preferably comprise the step of alerting the user to a scheduled medication event via an alert (e.g. a visual, an audible, and/or a tactile alert as generically depicted at arrow 101) according to the medication schedule (as at step or subroutine 119). The methodology may further preferably comprise the step of transmitting an alert cessation signal 102 to the medication compliance application for ceasing the alert signals 101 (as at step or routine 120) by removing the medication cap assembly 1 from the medication container 2 (as at step or subroutine 121).

The step of ceasing the alert by removing the medication cap assembly 1 from the medication container may further comprise the step of axially displacing the upper container rim 32 away from the wireless communication means as at arrow 104 thereby disengaging the wireless communication means from the mediation container 2 (as at step or subroutine 122).

Accordingly, although the invention has been described by reference to certain preferred and alternative embodiments, and methodology, it is not intended that the novel arrangements or methods be limited thereby, but that modifications thereof are intended to be included as falling within the broad scope and spirit of the foregoing disclosures, the appended claims and drawings.

We claim:

1. A medication compliance system, the medication compliance system for enhancing compliance of a user's medication regimen, the medication compliance system comprising in combination:

a medication compliance application, the medication compliance application being operable via a computing device; and a medication cap assembly, the medication cap assembly comprising an outer cap housing, an inner cap housing movable relative to the outer cap housing, and a circuit assembly for wirelessly communicating with the medication compliance application when the medication cap assembly is selectively interacted with a medication container;

the inner cap housing comprising lower housing surfacing and upper housing surfacing, the upper housing surfacing comprising at least one pocket construction, the circuit assembly comprising assembly components, the assembly components being located intermediate the inner cap housing and the outer cap housing, the at least one pocket construction for pocket-receiving select assembly components of the circuit assembly.

2. The medication compliance system of claim 1 wherein the medication compliance application alerts the user when medication is to be retrieved from a medication container via an alert, the alert being provided until the medication cap assembly signals the medication compliance application.

3. The medication compliance system of claim 1 wherein the inner cap housing and the outer cap housing are cooperable to position the circuit assembly relative to the medication container.

4. The medication compliance system of claim 3 wherein a button of the circuit assembly physically engages the medication container when the medication cap assembly is attached to the medication container.

5. The medication compliance system of claim 4 wherein the button of the circuit assembly engages the medication container via the inner cap housing when the medication cap assembly is attached to the medication container.

6. The medication compliance system of claim 2 wherein the circuit assembly transmits an alert cessation signal to the medication compliance application when the medication cap assembly is removed from the medication container.

7. The medication compliance system of claim 4 comprising in combination, the medication container, the medication container comprising an upper container rim, the upper container rim being engageable with the spring-biased button of the circuit assembly for signaling the medication compliance application.

8. A cap assembly, the cap assembly for enhancing compliance of a user's medication regimen, the cap assembly comprising:

an outer cap housing and an inner cap housing movable relative to the outer cap housing, the inner cap housing comprising lower housing surfacing and upper housing surfacing, the upper housing surfacing comprising at least one pocket construction; and a circuit assembly for wirelessly communicating with a medication compliance application and for signaling the medication compliance application when selectively interacted with a medication container, the circuit assembly comprising assembly components, select assembly components of the circuit assembly being configured intermediate the inner cap housing and the outer cap housing, the at least one pocket construction for pocket-receiving select assembly components of the circuit assembly.

9. The cap assembly of claim 8 wherein the upper housing surfacing comprises a series of post constructions, the series of post constructions being matable with a series of post-receiving structures cooperably associated with the circuit assembly for preventing movement of the circuit assembly relative to the inner cap housing.

10. The cap assembly of claim 9 wherein each post construction of the series of post constructions comprises an upper post portion and a lower spacer portion, the spacer portions for engaging the circuit assembly and spacing said circuit assembly from a planar portion of the upper housing surfacing.

11. The cap assembly of claim 9 comprising four post constructions, the four post constructions being equally spaced from each other at 90 degree intervals at a periphery of the upper housing surfacing.

12. The cap assembly of claim 11 wherein the upper housing surfacing comprises at least two pocket constructions, the at least two pocket constructions being respectively spaced intermediate a select three of the four post constructions.

13. The medication compliance system of claim 3 wherein the inner cap housing comprises a button-letting aperture, a button of the circuit assembly physically being extendable through the button-letting aperture for engaging the medication container via the inner cap housing when the medication cap assembly is attached to the medication container.

14. A medication compliance method, the medication compliance method for enhancing compliance of a user's medication regimen, the medication compliance method comprising the steps of:
   providing a medication compliance application, the medication compliance application being operable via a computing device; and
   providing a medication cap assembly, the medication cap assembly comprising an outer cap housing, an inner cap housing movable relative to the outer cap housing, and a circuit assembly for wirelessly communicating with the medication compliance application, the inner cap housing comprising lower housing surfacing and upper housing surfacing, the upper housing surfacing comprising at least one pocket construction, the circuit assembly comprising assembly components, select assembly components of the circuit assembly being configured intermediate the inner cap housing and the outer cap housing and received in the at least one pocket construction.

15. The medication compliance method of claim 14 comprising the steps of:
   a. outfitting a medication container with the medication cap assembly; and
   b. programming the medication compliance application with prescription medication regimen information.

16. The medication compliance method of claim 15 wherein the step of outfitting the medication container with the medication cap assembly comprises the step of depressing a switch button of the circuit assembly via the medication container.

17. The medication compliance method of claim 15 comprising the step of alerting the user to a scheduled medication event according to a medication schedule programmed into the medication compliance application.

18. The medication compliance method of claim 17 comprising the step of transmitting an alert cessation signal to the medication compliance application.

19. The medication compliance method of claim 18 wherein the step of transmitting an alert cessation signal to the medication compliance application comprises the step of axially displacing an upper container rim of the medication container away from a select component of the circuit assembly.

* * * * *